(12) United States Patent
Pazik

(10) Patent No.: US 11,607,534 B2
(45) Date of Patent: *Mar. 21, 2023

(54) CONNECTOR SYSTEM FOR MEDICAL FLUID ADMINISTRATION

(71) Applicant: THE ENTERPRISE CRADLE LIMITED, Aylesbury (GB)

(72) Inventor: Karol Pazik, Aylesbury (GB)

(73) Assignee: THE ENTERPRISE CRADLE LIMITED, Aylesbury (GB)

( * ) Notice: Subject to any disclaimer, the term of this patent is extended or adjusted under 35 U.S.C. 154(b) by 754 days.

This patent is subject to a terminal disclaimer.

(21) Appl. No.: 16/596,016

(22) Filed: Oct. 8, 2019

(65) Prior Publication Data

US 2020/0030594 A1 Jan. 30, 2020

Related U.S. Application Data

(63) Continuation of application No. 15/162,961, filed on May 24, 2016, now Pat. No. 10,485,965, which is a
(Continued)

(51) Int. Cl.
*A61M 39/10* (2006.01)
*A61M 39/22* (2006.01)

(52) U.S. Cl.
CPC .......... *A61M 39/10* (2013.01); *A61M 39/221* (2013.01); *A61M 2039/1061* (2013.01);
(Continued)

(58) Field of Classification Search
CPC .... A61J 1/1406; A61M 39/10; A61M 39/221; A61M 2039/1061; A61M 2039/1072; A61M 2039/1094
See application file for complete search history.

(56) References Cited

U.S. PATENT DOCUMENTS 4,936,841 A 6/1990 Aoki et al.
9,375,560 B2 * 6/2016 Pazik ............... A61M 39/10
(Continued)

FOREIGN PATENT DOCUMENTS

DE 3618158 12/1987
DE 29502544 6/1996
(Continued)

OTHER PUBLICATIONS

Japanese Office Action in corresponding Japanese Application No. 2013-503168 dated Feb. 17, 2015. (13 pages; English translation).
(Continued)

*Primary Examiner* — David Bochna
(74) *Attorney, Agent, or Firm* — Hamre, Schumann, Mueller & Larson, P.C.

(57) ABSTRACT

A connector system for medical fluid administration has a female connection member, which can act as an access port for a container of medical fluid, and a male connection member, for accessing the container of medical fluid. The female connection member defines a sheath for receiving a portion of the male connection member and this sheath is spanned at one end by a septum, which acts to close the container of medical fluid. A lumen is defined through the male connection member to allow passage of fluid therethrough. The septum has a central region and a peripheral region, the central region being of substantially greater thickness than the peripheral region. The male connection member comprises means for rupturing the peripheral region of the septum when it is received in the female connection member to form a connection.

12 Claims, 14 Drawing Sheets

Related U.S. Application Data continuation of application No. 13/639,951, filed as application No. PCT/GB2011/000544 on Apr. 7, 2011, now Pat. No. 9,375,560.

(52) U.S. Cl.
  CPC .............. *A61M 2039/1072* (2013.01); *A61M 2039/1094* (2013.01)

(56) References Cited

U.S. PATENT DOCUMENTS

| | | | |
|---|---|---|---|
| 10,485,965 B2* | 11/2019 | Pazik | A61M 39/10 |
| 2002/0020636 A1 | 2/2002 | Bergamini et al. | |
| 2005/0203484 A1 | 9/2005 | Nowak | |
| 2008/0086091 A1 | 4/2008 | Anderson et al. | |
| 2008/0249498 A1 | 10/2008 | Fangrow | |
| 2009/0292271 A1 | 11/2009 | Stepovich et al. | |
| 2009/0299325 A1 | 12/2009 | Vedrine et al. | |
| 2010/0004619 A1 | 1/2010 | Rondeau et al. | |
| 2015/0217104 A1* | 8/2015 | Biehl | A61M 39/10 604/500 |
| 2017/0258683 A1* | 9/2017 | Tsakas | A61J 1/1406 |

FOREIGN PATENT DOCUMENTS

| | | |
|---|---|---|
| EP | 0360471 | 3/1990 |
| EP | 1122186 | 8/2001 |
| EP | 2150307 | 10/2010 |
| JP | 02-134166 | 5/1990 |
| JP | 4-38955 | 4/1992 |
| JP | H04-38955 U | 4/1992 |
| JP | 2002-325850 | 11/2002 |
| JP | 2008-284343 | 11/2008 |
| KR | 10-2004-0095276 | 11/2004 |
| WO | 2008/144447 | 11/2008 |

OTHER PUBLICATIONS

Japanese Office Action, issued in the corresponding Japanese application No. 2018-116935, dated May 14, 2019, 7 pages.
Indian Examination Report, issued in the corresponding Indian application No. 9546/DELNP/2012, dated Sep. 23, 2019, 6 pages.
Japanese Office Action, issued in the corresponding Japanese application No. 2018-116935, dated Jan. 21, 2020, 14 pages including English translation.

\* cited by examiner

SECTION A-A

SECTION B-B

SECTION A-A

CONNECTOR SYSTEM FOR MEDICAL FLUID ADMINISTRATION

The invention relates to a connector system suitable for medical fluid administration. In particular the invention may relate to male and female elements of a connector, and a connector system comprising the male and female elements suitable for allowing access to containers containing medical fluids, to enable delivery of the medical fluids to a patient.

BACKGROUND

Medical fluids intended for parenteral administration to a patient are typically supplied in solid containers such as vials and infusion bottles, or in collapsible bags, for example IV bags. At present these containers typically come with universally standardised necks and closure systems that conform to DIN standards. These containers are typically accessed either by hypodermic needles or spikes fitted to administration equipment in order to allow passage and administration of the fluid contained within. Medical fluids include medical suspensions and solutions, and biological liquids such as blood and plasma.

Products intended for parenteral administration may be intended for administration to different parts of the body and to different circulatory systems within the body. For example, some products and fluids are intended for intravenous delivery into the patient's blood system, whereas other products and fluids are intended for delivery to spinal fluids. It is extremely dangerous to administer products to the wrong system and, unfortunately, a number of patient fatalities have occurred as a consequence of the erroneous delivery of an epidural product to the blood system, and vice versa.

At present, health care professionals tend to rely on visual cues to ensure that a particular product is not administered incorrectly. However, it may be difficult in many situations for a health professional to track fluid tubing or conduits to confirm the route of entry into the body; especially where a patient is immobilised and those routes of entry are hidden beneath the patient.

Considerable work has been undertaken to differentiate the equipment and administration sets for the epidural administration of products from equipment and administration sets for intravenous administration of products. However, such work has focused on the architecture of the equipment and the administration sets downstream of the connector used to connect to the product. Because there is no differentiation between containers of epidural products and intravenous products, and because there is no differentiation of the connector on the equipment and administration set to connect to the product, the risk of a potentially fatal crossover remains at the product container-connector interface.

It is the aim of the invention to provide a connector or connector system for medical fluid administration that can be readily incorporated into the seals of standard product containers such that containers holding fluids intended for a specified route of delivery may be physically differentiated from containers holding other fluids that are incompatible with that route of delivery. For example, it is an aim that containers containing fluids for epidural administration are physically incapable of connection to any current universal administration sets and apparatus for delivery of intravenous fluids.

SUMMARY OF THE INVENTION

The invention provides in its various aspects a connector system, a male connection member, and a female connection member for medical fluid administration and a method of making a connection as defined in the appended independent claims, to which reference should now be made. Preferred or advantageous features of the invention are defined in various dependent sub claims.

Thus, in a first aspect the invention may provide a connector system or coupling system for medical fluid administration comprising a male connection member having a first or distal portion terminating in a first or distal end and a second or proximal portion terminating in a second or proximal end. A lumen is defined through the male connection member for the passage of liquid from the distal end to the proximal end. The connector system further comprises a female connection member defining a sheath for receiving the distal portion of the male connection member. A first or distal end of the sheath is spanned by a septum, the septum for preventing flow of liquid through the female connection member. A first or central region of the septum is formed from material having a substantially greater thickness than a second or peripheral region of the septum surrounding the central region. If the septum is circular then the radially outermost portions of the septum (i.e. the peripheral region) are preferably substantially entirely formed from a thinner section of material and the central region of the septum will be formed from a thicker section of material. The distal end of the male connection member comprises means for rupturing the peripheral region of the septum when the male connection member is inserted or received in the female connection member to form a connection.

Thus, the female connection member of the system may form an access port or an opening to a container containing liquid, for example a medical fluid, and engagement with the male connection member of the system allows the septum of the female connection member to be ruptured thereby resulting in fluid flowing through the lumen of the male connection member.

One way in which standard giving set spikes and hypodermic needles are able to access medical fluids is by being pushed through a septum of a closure or an access port, which then forms a seal around the barrel of the needle or spike. The lumen of the spike or needle is typically central and concentric to the axis of the instrument and is typically at the point of the instrument such the fluid flows through the centre of the puncture site.

By utilising a septum that has material of a greater thickness in a central region, compared with the thickness in peripheral region surrounding the central region, then the septum becomes more resistant to puncture by a standard giving set spike or by a hypodermic needle. A healthcare professional attempting to insert a standard spike or hypodermic needle into the female connection port of the connector system would encounter a resistance to the insertion of the spike or needle due to the thickness of material at the central region. This may be sufficient warning for the healthcare professional to realise that an inappropriate connection is being attempted.

Should the healthcare professional persist by attempting to force the spike or needle through the septum then the septum will rupture preferentially at the peripheral region, where the material is thinner than in the central region. This prevents the septum from forming a seal around the barrel of the needle or spike resulting in leakage of fluid from the container. Thus, an incompetent or unsound connection is formed, preferentially with a dislocation between the receiving lumen of the needle or spike and the rupture created in the septum, preventing fluid from being delivered from the container to the administration system.

The central region may be between 1.5 and 400 times thicker than the material forming the peripheral region of the septum. Preferably the central region of the septum is between and 2 and 20 times thicker than the material forming the peripheral region of the septum, particularly preferably between 3 and 10 times, or 4 and 8 times thicker. The ratio of the thicknesses may depend on the type of material used for the septum. The ratio of thicknesses should be such that the material in the peripheral region of the septum is thick enough to maintain a competent seal retaining the fluid within the container but not so thick as to allow a needle or spike to be pushed through the central region of the septum without the peripheral region bursting.

Preferably the material in the peripheral region of the septum is thin enough to prevent a seal forming around the barrel of a needle or spike having a similar cross-sectional diameter to the thickness of the material forming the peripheral region. Thus, if such a needle or spike is inserted off-axis through the peripheral region of the septum, a competent seal is unlikely to form. A needle or spike that has substantially greater diameter compared to the thickness of the material forming the peripheral region is likely to catastrophically rupture the septum, which will also prevent a seal from being formed.

Preferably the peripheral region is a substantially annular region surrounding a substantially circular central region of the septum. The peripheral region may not form a complete ring around the circular central region, but should extend sufficiently to result in a catastrophic failure around the periphery of the septum in preference to a puncture through the central region of the septum.

For some applications it may be desirable that the central region of the septum does not easily become detached from the female connection member and, consequently, fall into a container that is closed by the female connection member. Thus, it may be advantageous for the central region to be connected to the distal end of the sheath by a suitable retaining means or retaining member to prevent complete detachment of the central region when the peripheral region is disrupted or ruptured. Such retaining means may comprise a section of material connecting the central region of the septum to the distal end of the sheath such that the central region remains attached to the sheath after the peripheral region has been disrupted. The retaining means or retaining member may effectively be a hinge, or act as a hinge, allowing the central region to pivot, thereby allowing access to a container through the septum, while retaining the central region in physical connection with the female connection member so that it does not fall into the container.

In a preferred configuration, a retaining means may comprise a section of material or a web of material extending radially between the distal end of the sheath and the central region of the septum. In some embodiments, a lug, flange or tab may project longitudinally from the distal end of the sheath and the section of material or web of material may extend radially from this lug, flange or tab to connect with the central region of the septum.

In an alternative preferred configuration, the connector system may be adapted such that the peripheral region is not disrupted around its full circumference. Thus, after the peripheral region has been disrupted a portion of the peripheral region may remain to act as both a hinge and a retaining means for retaining the central region of the septum. For example, the connector system may be configured such that only between 340 degrees and 355 degrees of the circumference of the peripheral region are disrupted so that the remaining 5 to 20 degrees act to retain the central portion while still allowing a fluidic connection to be formed. A preferred method of achieving such a configuration may involve the use of a key on the male connection member that is engageable with a keyway defined in a female connection member. The keyway allows the male connection member to be rotated within the female connection member through a defined angle. This is described below in more detail.

It is preferable that the female connection member of the connector system is dimensioned to fit standard medical vials, bottles, and bags. Thus, the central region of the septum preferably has a width or diameter of between 5 mm and 10 mm, for example in the region of 7 mm or in the region of 8 mm.

The material forming the central region has preferred thickness of between 1 mm and 3 mm, preferably in the region of 2 mm. The thickness of the central region will depend on the material properties of the material used to form the septum.

The material forming the peripheral region has a preferred thickness of between 0.1 mm and 1.5 mm, depending on the thickness of the central region. The peripheral region may have a thickness of between 0.2 mm and 0.6 mm, for example about 0.25 mm.

Furthermore, the overall diameter of the septum is preferably in the range of between 8 mm and 15 mm, for example about 11 mm or 12 mm. As the diameter of the septum is substantially the same as the internal diameter at the distal end of the sheath, it is noted that the distal end of the sheath has an internal diameter of preferably between 8 mm and 15 mm.

A standard intravenous giving set spike has a tapered body, which allows a second method of forming a connection with a container. Collapsible bags containing medical fluid are often sealed by an access port having a tapering barrel for receiving the body of the spike. The interference between the body of the spike and the tapering barrel provides a fluid-tight seal that allows the fluid to be delivered through the spike.

In the connector system of the present invention, the seal is provided by interference between the distal portion of the male connection member and the internal surface of the sheath. In order to prevent a standard intravenous spike from forming a seal with the female connection member of the connector system, the internal diameter of the sheath, and therefore the external diameter of the distal portion of the male connection member (i.e. the mating portion of the male connection member), is preferably greater than that of a standard intravenous spike. In this configuration it is not possible to form an inadvertent connection by inserting an intravenous spike into a female connection member of a connector according to an aspect of the present invention.

Preferably at least a portion of the sheath is tapered, such that a proximal end of the sheath is of greater diameter than the distal end of the sheath. Where the sheath is tapered, then the distal portion of the male connection member will be similarly tapered in order to mate with the female connection member. This tapering may facilitate the engagement of the male connection member and the female connection member. The angle of the taper is preferably between 0.5° and 3.5°, for example between 1° and 2°. A preferable angle of taper is about 1.5°.

It may be advantageous for a portion of the sheath, and therefore a portion of the distal portion of the male connection member, to be substantially parallel-sided. If the proximal end of the sheath has substantially parallel walls, and the distal end of the sheath has tapered walls, then a seal may be made between the male connection member and the sheath, by the mating of the respective parallel portions, prior to the engagement of the distal end of the male connection member with the septum. Thus, a liquid tight seal may be formed prior to the rupturing of the septum, thereby preventing any initial leakage.

It is preferred that the female connection member may be used to form a closure or an access port for standard medical fluid containers. Thus, it is preferable that the female connection member comprises a substantially annular flange extending radially outwards from the sheath enabling the female connection member to span an opening of a container. The flange may further comprise features such as ridges and lugs for facilitating connection of the female connection member to a container.

Preferably the male connection member forms a giving set spike for the administration of medical fluids. Preferably the female connection member forms an access port into a container for containing medical fluids, for example an IV bag an infusion bottle, or a vial.

It is preferable that, if used for the administration of medical fluids, the connector is consistently used for a single type of medical fluid. For example, it is preferable that the male connection member is only used as a giving set spike on administration sets for supplying epidural fluid. In this situation, it is important that the female connection member of the system is only used as an access port for containers holding epidural fluids. Thus, the consistent use of this one type of connector system may make it extremely difficult for a healthcare professional to accidentally administer an epidural fluid into a patient's vascular system.

It may be advantageous that the means for rupturing the septum comprises a projection, or more than one projection, located on the distal portion of the male connection member and that this protection is aligned for engagement with the peripheral region of the septum when the male member is received within the female member. It may be advantageous that the first contact between the male connection member and the septum is made by the projection on the peripheral region of the septum. Thus, the projection may form the distal extremity of the male connection member and the projection may be located such that it aligns with the peripheral region of the septum when the male member is engaged with the female member.

Preferably, in a connector system or a male connection member for medical fluid administration the projections extend for a distance of between 0.5 mm and 6 mm from the distal end of the male connection member. Particularly preferably the projections extend for a distance of between 1 mm and 5.5 mm or between 2 mm and 5 mm, for example about 3 mm or 4 mm.

For some applications it may be preferred that the projections only extend a short distance from the distal extremity of the male connection member. For example the projections may only extend between 0.5 mm and 2 mm, for example 1.25 mm or 1.5 mm or 1.75 mm. This may be an advantage if the female connection member comprises retaining means, such as a hinge, for retaining the central region of the septum after rupture of the peripheral region of the septum. Thus, it may be preferred that the projections are long enough to rupture or disrupt the peripheral region of the septum, but are not long enough to rupture or break a retaining means for retaining the central region of the septum.

It may be particularly advantageous if the male connection member comprises two or more projections located on the distal portion of the male connection member that the two or more projections are aligned for engagement with the peripheral region of the septum. The projections may be arranged such that they all contact the septum simultaneously on engagement between the male connection member and the female connection member or the projections may be of different lengths such that one or more of the protections engages with the septum before the others. It may be advantageous that, where there is more that one projection, the projections are circumferentially evenly spaced around the distal end of the male connection member. Alternatively, in some configurations it may be preferred that the projections are not circumferentially evenly spaced around the distal end of the male connection member.

It may be particularly advantageous that any projection located on the male connection member terminates in a tooth, an edge, for example a knife edge, or spike for rupturing the peripheral region of the septum. Such rupturing means may facilitate the breach of the septum, particularly where the thinned portion of the peripheral region of the septum needs to retain some strength in order to retain the desired volume of the liquid in the container.

A tooth-edge or spike may be of particular efficacy in rupturing the peripheral region of the septum if the male connection member is rotated or twisted when brought into contact with the septum. Thus, a knife edge may form a circumferential slice around the peripheral region of the septum when pressed into the septum and twisted. Likewise, a tooth, such as a saw-tooth, may advantageously cut into and disrupt the peripheral region of the septum when engaged with the septum and twisted.

It may be of particular advantage that any rupturing means on a projection such as a tooth, edge, or spike is oriented such that any cutting or rupturing advantage associated with rotating the male connection member is obtained whichever way the connection member is rotated, i.e. whether it is rotated clockwise or anti-clockwise. Thus, the connector system may be used by both right and left handed people with equal ease of forming a connection. As an example, a knife edge may be substantially triangular such that it cuts whether rotated in an anti-clockwise or a clockwise direction. Where saw teeth are used it is preferable that at least two saw teeth are used and that these saw teeth are arranged to face each other so that one tooth cuts more efficiently if the male connection member is rotated in a clockwise direction and the other cuts more efficiently if the male connection member is rotated in an anti-clockwise direction.

A male connection member comprising a projection or a plurality of projections may be twisted after engagement with a female connection member so that the projection or projections travel circumferentially around the peripheral region, thereby disrupting the peripheral region. If there is no means for restricting the circumferential motion of the male connection member relative to the female connection member (as caused by twisting after engagement), the projection or projections may be capable of rupturing the entire peripheral region. For example, if the male connection member comprises a single projection that is aligned with the peripheral region of the female connection member after engagement, twisting the male connection member through 360 degrees relative to the female connection member will result in the entire peripheral region being disrupted. Alternatively, if the male connection member has two projections circumferentially spaced at 180 degrees from each other, the male member only needs to be twisted by 180 degrees relative to the female connection member for the entire peripheral region to be disrupted.

Advantageously, the connector system may comprise a means for restricting the angle through which a male connection member may be twisted relative to a female connection member. When coupled with an appropriate configuration of projections, such a system may help to prevent the peripheral region from being disrupted around its entire circumference, and may, therefore, help retain the central region in contact with the female connection member after a connection has been made. The means may be formed by an element on the male connection member that interferes with an element on the female connection means thereby restricting the range of rotation between the two connection members. In a preferable configuration the male connection member comprises a key formed on its distal portion and the female connection member comprises a keyway for receiving the key defined in its sheath. The keyway extends around a portion of the circumference of the sheath so that the male connection member may be circumferentially rotated after engagement. The interaction of the key and the keyway, however, prevents the male connection member from being rotated through 360 degrees.

Where a connector system includes a key and a keyway to restrict rotation of the male connection member, the angle by which this rotation is allowed will depend on the configuration of projections on the male connection member. If there is only a single projection, for example, rotation may be allowed through an angle of up to 355 degrees to effect a 355 degree disruption to the peripheral region. If, alternatively, the male connection member includes two projections circumferentially spaced from each other by an angle of 100 degrees, rotation of only 255 degrees may result in a 355 degree disruption to the peripheral region.

Preferably any key on a male connection member only partially extends along a distal portion of the male connection member. Likewise, it is preferable that any keyway defined in a female connection member only partially extends into the sheath. Thus, mating surfaces of the male connection member and the female connection member form a liquid-tight seal.

The purpose of the male connection member is to form a connection by a catastrophic rupture of a peripheral region of the septum of a female connection member. To facilitate this it may be advantageous that the projection or, where there is more than one projection, each projection is shaped to deflect the central region of the septum on engagement between the male and female connection members. Thus the projections may be shaped to act as wedges and deflect the central region of the septum away from the wall of the sheath. Such deflection may increase the stress on any remaining portions of the peripheral region of the septum and may accelerate the catastrophic failure of the septum, thereby forming the connection. Thus, the projections may be inclined circumferentially and/or radially in order to provide a deflection of the central region of the septum.

If the female connection member comprises a retaining means or retaining member for retaining the central region of the septum, it is preferred that interaction between the male connection member and the female connection member results in disruption of the peripheral region of the septum but does not rupture the retaining means or retaining member. Additionally or alternatively, the peripheral region may not be completely disrupted around its entire circumference. In these embodiments it is preferred that the central region is opened or deflected to allow access through the septum, but is retained in contact with the female connection member.

It may be advantageous that the lumen, which extends through the male connection member in order to allow liquid to flow when the connection has been formed, is flared at the distal end of the male connection member. Thus it may be advantageous that the lumen forms a funnel-like shape at the distal end. This funnel or depression may advantageously act to channel liquid towards the central portion of the lumen extending through the remainder of the connector.

The male connection portion of the connector system may have a number of features that help prevent accidental connection with a standard IV connection port. For example, if the male connection member is inserted into the rubber septum of a standard DIN bung for a bottle or vial then the means for rupturing the peripheral region of the septum is highly unlikely to penetrate the bung. The means for rupturing the peripheral region of the septum of the female connection member is likely to merely deflect the highly resilient material that is typically used for a bung. If the male connection member has projections that extend from the distal end of the male connection member, these projections are likely to elastically deform the bung material. Apart from the means for rupturing, for example a projection, the distal end of the male connection member is preferably blunt. Thus, the distal end acts as a stop, preventing a standard DIN bung from being ruptured. In the unlikely event that the male member was capable of rupturing a standard DIN bung, the lumen of the member would not be aligned with the breach of the septum and no fluid would be allowed to flow through the connector.

It is preferred that the physical dimensions of the male connection member are such that it cannot mechanically fit into an access port of a standard collapsible bag, as used for the access of universal giving set spikes. This may add a further level of security making it unlikely that the male connector can be connected to standard access ports.

The male connection member needs to be inserted longitudinally into the female connection member, and may also need to be twisted. To facilitate insertion into the female member it may be advantageous for the male connection member to comprise a lug or flange located between the distal portion and the proximal portion of the male connection member. For example, the male connection member may comprise a radial flange, possibly a radial flange extending entirely around the circumference of the male connection member. This flange may be used to apply a force in the longitudinal direction to insert the male connection member into the female connector. The flange may additionally serve to provide a stop on the male connection member to indicate that it has been inserted the required distance into the female member to form a connection.

Where the male connection member is designed to be twisted it may be advantageous for the proximal portion of the male connection member to be ergonomically adapted to facilitate a user to grip the male connection member and twist the connection member. To this end it may be advantageous to shape this portion of the male connection member with ridges or knurls to facilitate grip. It may be particularly advantageous that the proximal portion of the male connection member comprises one or more longitudinal flanges that extend along a proximal portion of the member. Such flanges may be used to apply a twisting motion to the male connection member.

The proximal end of the male connection member may be couplable to any required device or conduit or tubing to allow liquid flowing through the connection to be used for the desired purpose.

It is desirable that the male portion of the connector system is associated with tubing and administration sets for administration of a certain species of medical fluid, for example for the administration of epidural fluids. It is also preferable that the female portion of the connector system is associated with containers for containing the same particular species of medical fluid, for example epidural fluids.

Thus, the invention may provide a male connection member, or male connector, for a connector system for medical fluid administration as described above.

The invention may also provide a female connection member, or female connector, for a connector system for medical fluid administration as described above. Additionally, the invention may provide containers for medical fluids incorporating a female connection member for a connector system for medical fluid administration as described above.

In a second aspect, the invention may provide a method for making a connection between a male connection member defining a lumen for the passage of fluid and a female connection member defining a sheath for receiving a portion of the male connection member and having a distal end of the sheath spanned by a septum comprising a central region having material of substantially greater thickness than a peripheral region surrounding the central region comprising the steps of, inserting the portion of the male connection member into the female connection member, rupturing the peripheral region of the septum, and forming a liquid tight seal between the outer surface of the male connection member and an inner surface of the sheath.

It may be advantageous that the dimensions of the male connection member and the female connection member allow the steps of rupturing the septum and forming a seal to occur at substantially the same time in order to minimize leakage of fluid that may occur during the process of forming the connection.

Advantageously, the male connection member may be rotated or twisted on insertion into the female connection member. This twisting action may facilitate the disruption of the peripheral region of the septum.

Particularly advantageously, the distal end of the male connection member comprises projections that are aligned to engage with the peripheral region of the septum. These projections engage with the peripheral region of the septum and facilitate the disruption. Projections may be particularly efficacious if combined with the step of twisting the male connection member on insertion into the female connection member thus allowing projections to disrupt the peripheral region of the septum.

In a preferred method, the male connection member may incorporate a key that extends radially out ward of a distal portion of the male connection member and this key may mate with a keyway defined in the female connection member to allow the male connection member to be inserted into the female connection member. Preferably, the keyway restricts the extent of rotation or twisting of the male connection member within the female connection member to a predetermined maximum angle.

The connector system described in relation to the first aspect has two elements; a male connection member and a female connection member. In certain circumstances, these two elements may be advantageously supplied separately. For example, it may be advantageous that the male connection members are associated with tubing and administration sets for delivery of a medical fluid and female connection members may be associated with containers of medical fluids.

A third aspect of the invention, therefore, may provide a male connection member for a connector system for medical fluid administration. The male connection member of this aspect of the invention comprises a distal portion terminating in a distal end and a proximal portion terminating in a proximal end. A lumen is defined through the male connection member for the passage of liquid from the distal end to the proximal end. The distal end of the male connection member comprises means for rupturing a septum of a female connection member when the distal portion of the male connection member is inserted into or received within the female connection member to form a connection, the means for rupturing being located at a radially outermost portion of the distal end of the male connection member. It is preferable that the distal portion of the male connection member is of substantially circular cross-section. In this case the means for rupturing the septum will be located closer to the circumference of the distal end than the geometrical centre of the distal end.

The male connection member of the third aspect of the invention is preferably a male connection member for any connector system as described above in relation to the first aspect.

A fourth aspect of the invention may provide a female connection member for a connector system for medical fluid administration. The female member comprises a body defining a sheath for receiving a portion of a male connection member. A distal end of the sheath is spanned by a septum, the septum being for preventing flow of liquid through the female connection member. A central region of the septum is formed from material having a substantially greater thickness than a peripheral region of the septum surrounding the central region. If the septum is circular then radially outermost portions of the septum will be formed from a thinner section of material and the central portion of the septum will be formed from a thicker section of material.

The female connection member of the fourth aspect of the invention is preferably a female connection member for any connector system as described above in relation to the first aspect.

Male and female connection members or connectors as described in relation to any aspect of the invention described above are preferably manufactured from a polymer, particularly preferably a medical grade polymer. Different materials may be used depending on factors such as mechanical properties and chemical resistance. As non-limiting examples, the elements forming the connection system may be made from, or comprise, polypropylene (PP), polyethylene (PE), high density polyethylene (HDPE), polycarbonate (PC), polystyrene (PS), polyethylene terephthalate (PET), or acrylonitrile butadiene styrene (ABS), or any similar polymer or co-polymer material.

Male connection members of a connection system according to any aspect described above may be available in various configurations allowing the proximal portion of the connection member to be connected to different types of administration apparatus and different widths of tubing. Likewise, female connection members of the system may have various configurations allowing them to be coupled to, and used as access ports for, different types of fluid containers. The invention provides that any male connection member within the system can connect with any female connection member within the system. Thus, it may be particularly desirable that female connection members as described in relation to any aspect of the invention are used to provide access ports to a range of containers containing fluids for epidural administration. The exact configuration of the female members will vary, depending on whether the access port is in a collapsible bag, or a bottle, or a vial. However, all of these different containers will preferably be able to connect to an epidural administration set that comprises a corresponding male connection member as described in relation to any aspect of the invention.

SPECIFIC EMBODIMENTS OF THE INVENTION

Specific embodiments of various aspects of the invention will now be disclosed with reference to figures in which.

Figure 1:
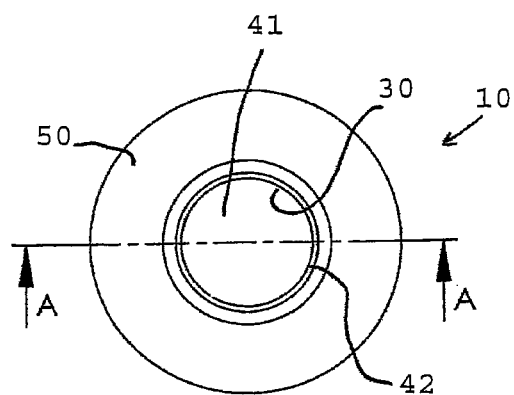
FIG. 1 illustrates a plan view of a first embodiment of a female connection member for a connector system for medical fluid administration.
Figure 2:
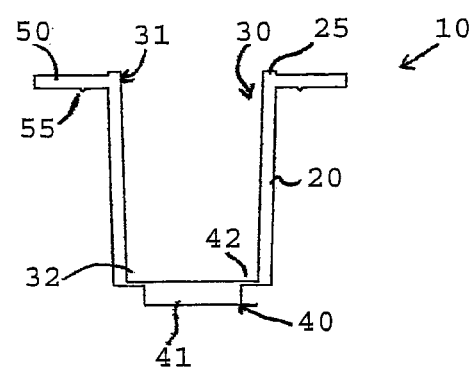
FIG. 2 illustrates a cross section of the female connection member of FIG. 1.

FIGS. 1 and 2 illustrate a first embodiment of a female connector or female connection member 10. The female connection member 10 may be used as a component in an embodiment of a connector system for medical fluid administration.

The female connection member 10 has a body 20 formed from a single moulding of polypropylene. The body 20 defines a sheath 30 having a substantially circular cross section. A proximal end of the sheath 31 defines an opening for receiving a male connection member and a distal end of the sheath 32 is spanned by a septum 40. An annular flange 50 extends radially outwards from an uppermost or proximal end of the sheath.

The septum 40 comprises two distinct portions. A central region or central portion 41 formed from a thick section of polypropylene and a peripheral region or peripheral portion 42 formed from a thin section of polypropylene. The internal diameter of the sheath at its proximal end is slightly greater than the internal diameter of the sheath at its distal end 32 resulting in a tapering of 1.5 degrees to the walls of the sheath. The polypropylene at the thickened central portion of the septum 41 has a thickness of 1.9 mm. The polypropylene at the peripheral thinner portion 42 has a thickness of 0.25 mm. The locating flange 50 has an annular ridge 55 on it's underside for facilitating sealing against a rubber washer or grommet.

Figure 3:
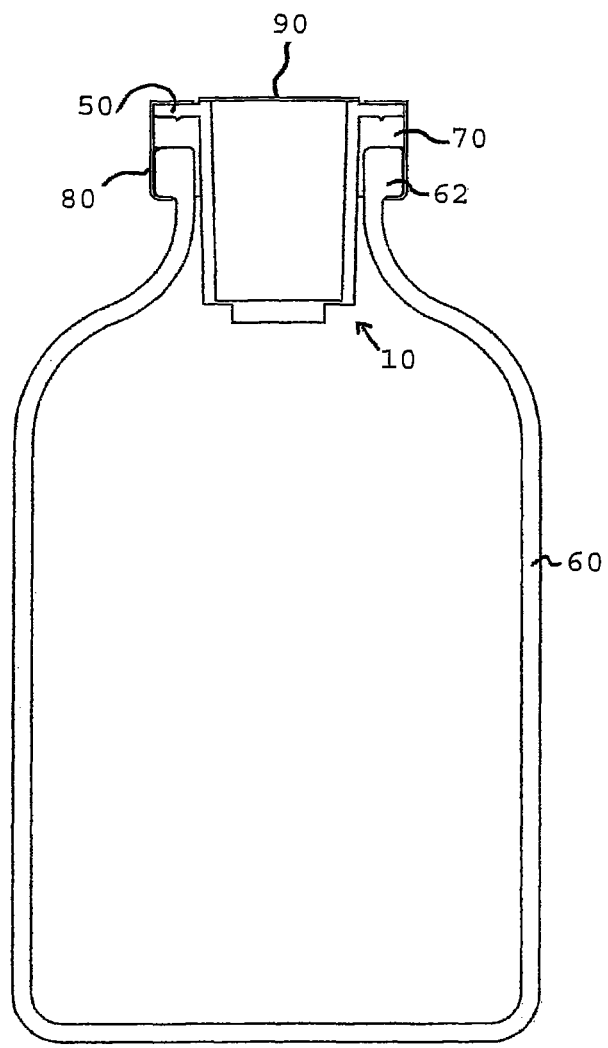
FIG. 3 illustrates the female connection member of FIG. 1 when used as an access port for a medical vial.

FIG. 3 illustrates the female connection member of FIGS. 1 and 2 located in a vial of medical fluid 60. The glass rim 62 of the vial 60 has an outer diameter of 20 mm. A rubber washer or grommet 70 fits into the neck of the vial 60 and provides a seat for the flange 50 of the female connection member 10. In order to locate the female connection member 10 within the neck of the vial and in order to provide a liquid tight seal, the flange 50 of the connection member 10 is compressed against the rubber washer 70 by an aluminium over-seal 80.

The aluminum over-seal 80 compresses the flange 50 into the rubber washer 70 and the annular ridge 55 on the under side of the flange 50 grips the rubber washer 70 providing additional seal competence. The female connection member 10 is provided with a removable seal 90 that is ultrasonically welded to a circumferential rim 25 of the sheath. This seal 90 prevents contamination to the inner surfaces of the sheath. It is noted that any known method of hermetically affixing a foil or cover to produce such a seal could be used.

The female connection member thus provides a closure for the vial 60 that prevents unwanted egress of fluid contained within the vial. Containers for medical fluid administration come in different sizes. It is possible to adapt a female connector member according to the invention such that it can be used to close different dimensions of medical administration containers.

Figure 4:
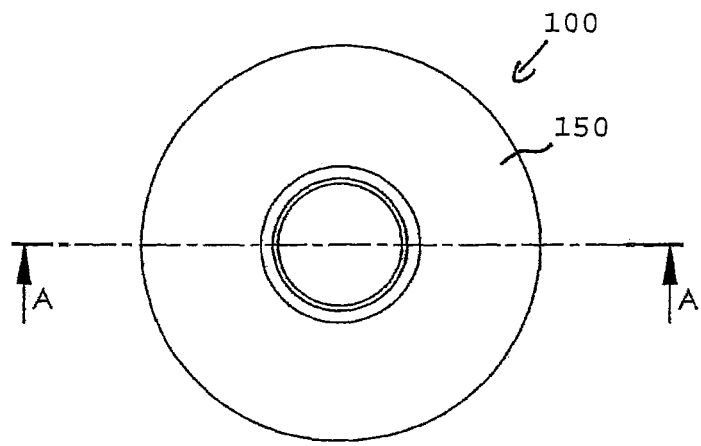
FIG. 4 illustrates a plan view of a second embodiment of a female connection member for a connector system for medical fluid administration.
Figure 5:
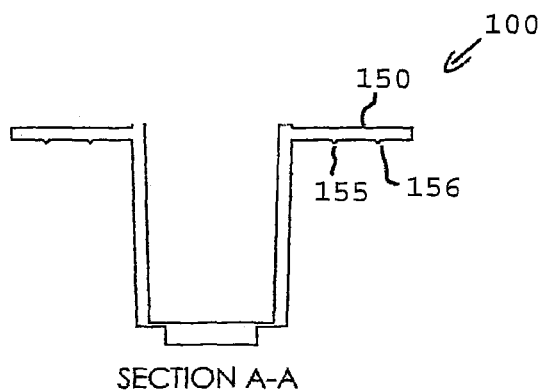
FIG. 5 illustrates a cross section of the female connection member of FIG. 4.
Figure 6:
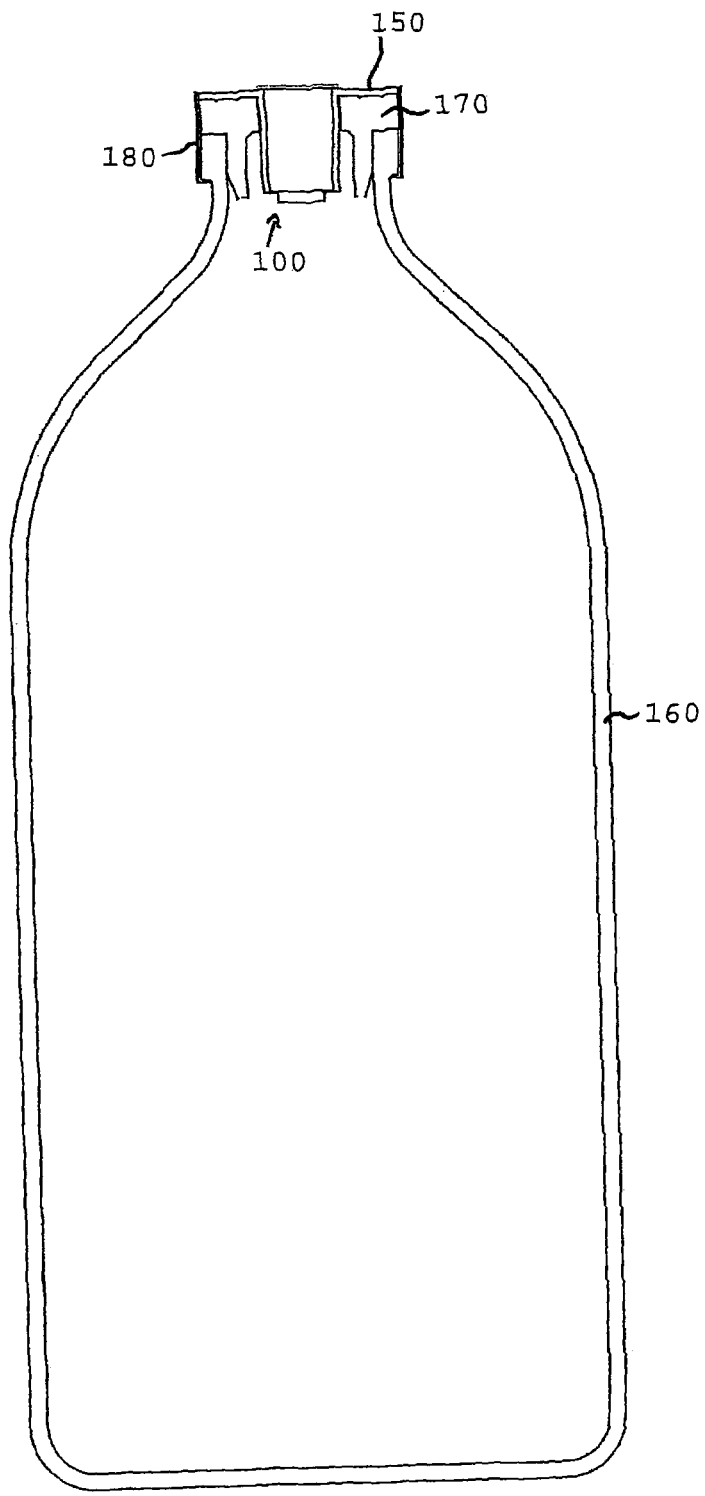
FIG. 6 illustrates the female connection member of FIG. 4 when used as an access port for a medical bottle.

FIGS. 4, 5 and 6 illustrate a second embodiment of a female connector or female connection member 100. The female connection member 100 may be used as a component in an embodiment of a connector system for medical fluid administration.

The female connection member 100 of FIGS. 4, 5, and 6 is designed to act as a closure for a large fluid container. The sheath and septum of the female connection member are constructed and dimensioned as disclosed for the embodiment illustrated in FIGS. 1, 2 and 3. The connection member has been adapted, however, in that a radially extending flange 150 extends for a diameter of 32 mm (rather than 20 mm as described above). Furthermore, the flange incorporates two concentric annular ridges 155 and 156.

FIG. 6 shows how this female connector 100 is used as an access port for a medical fluid container. A rubber T-section washer 170 fits within a standard 32 mm neck of the container 160. The 32 mm diameter flange 150 is compressed against the rubber T-section washer 170 by an aluminum over-seal 180. In the configuration shown, the two annular ridges 155 and 156 dig into the rubber T-section washer 170 in order to improve the competence of the seal.

Figure 7:
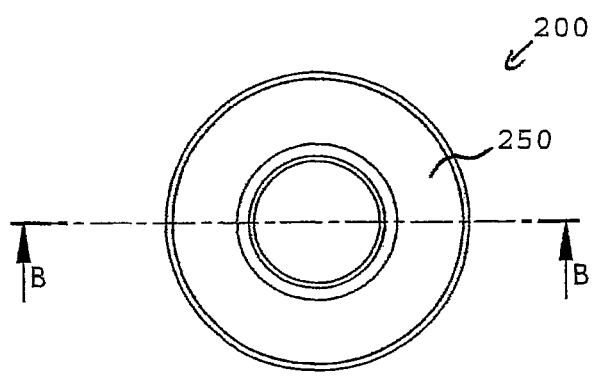
FIG. 7 illustrates a plan view of a third embodiment of a female connection member for a connector system for medical fluid administration.
Figure 8:
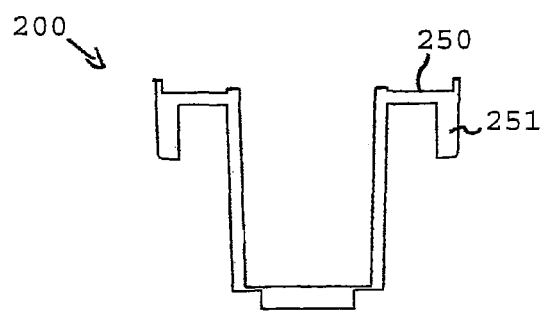
FIG. 8 illustrates a cross section of the female connection member of FIG. 7.
Figure 9:
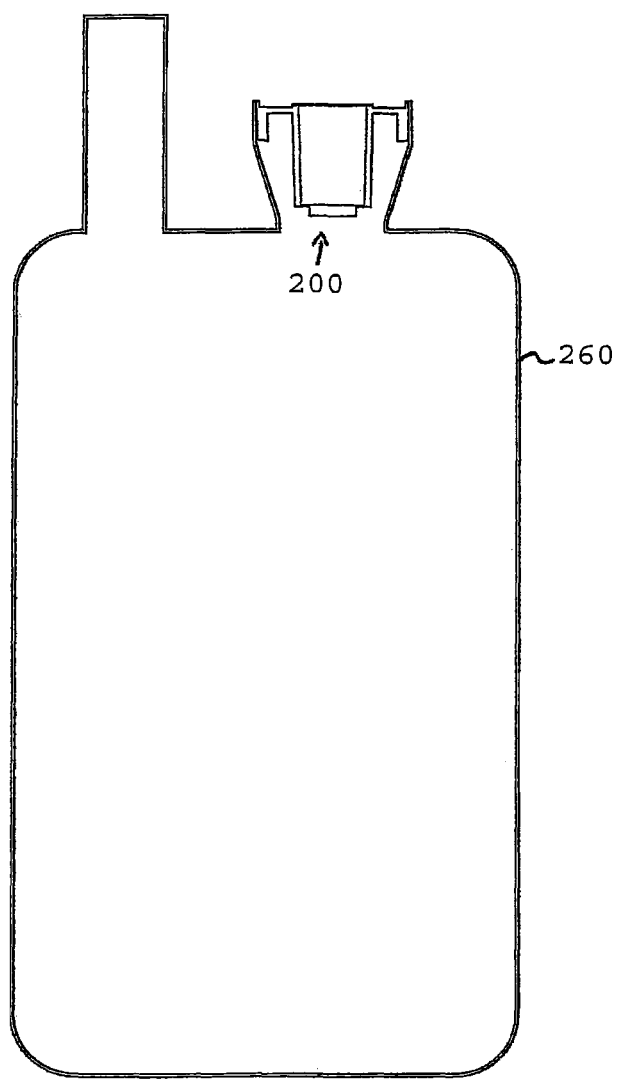
FIG. 9 illustrates the female connection member of FIG. 7 when used as an access port for a collapsible medical fluid bag.

FIGS. 7, 8 and 9 illustrate a third embodiment of a female connector or female connection member 200. The female connection member 200 may be used as a component in an embodiment of a connector system for medical fluid administration.

The dimensions of the sheath and septum are identical to the connection member described in relation to FIGS. 1 and 2. In the case of the connection member 200 of FIGS. 7 and 8, a flange is provided having an annular rim 251 designed to facilitate connection by adhesion or welding to a polypropylene infusion bag 260.

FIG. 9 illustrates the female connection member 200 as an access port for a polypropylene infusion bag 260.

The three different examples of a female connection member 10, 100, 200 described above have common dimensions of a sheath for receiving a male connection member and a septum spanning a distal portion of the sheath. All three female connection members may be accessed by a common male connection member.

Figure 10:
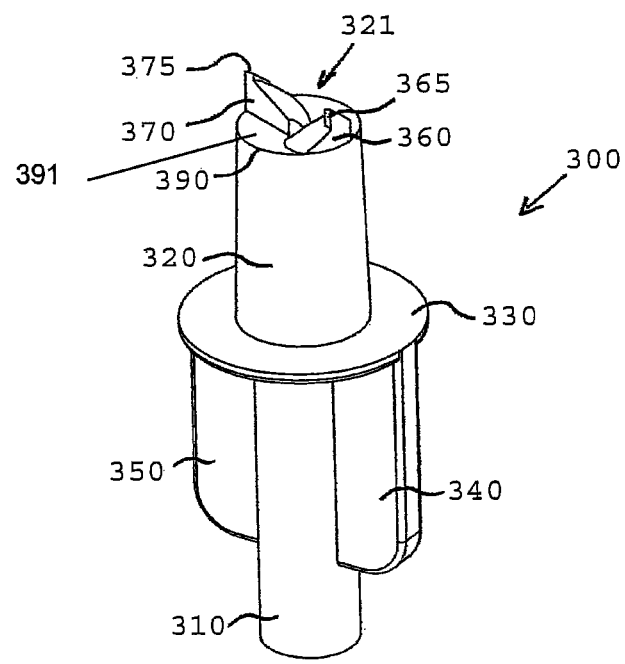
FIG. 10 is a perspective illustration of a first embodiment of a male connection member for a connector system for medical fluid administration that is compatible with any of the female connection members illustrated in FIGS. 1 to 9.
Figure 11:
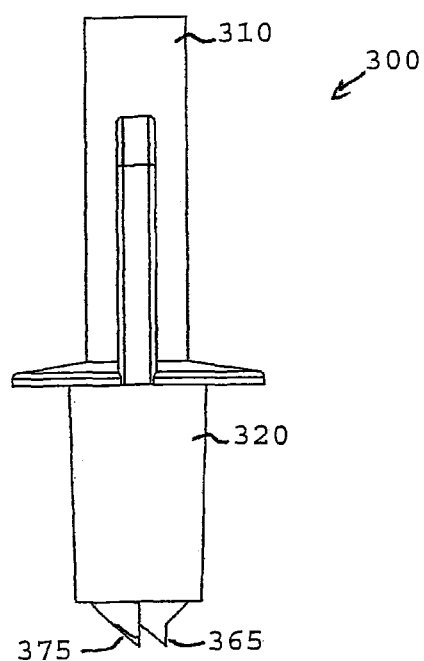
FIG. 11 is a side view of the connector of FIG. 10.
Figure 13:
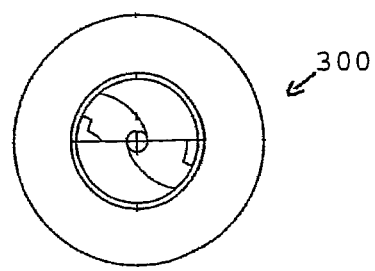
FIG. 13 is a bottom view of the connector of FIG. 10.
Figure 12:
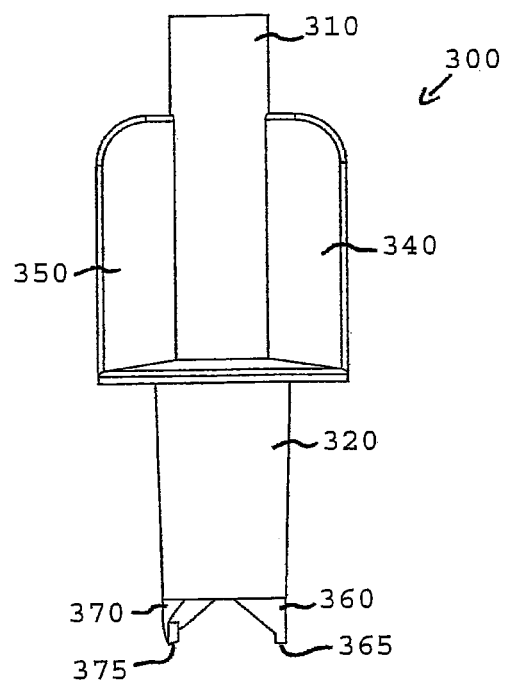
FIG. 12 is a front view of the connector of FIG. 10.

FIGS. 10, 11 and 12 illustrate a first embodiment of a male connector or male connection member 300. The male connection member 300 may be used as a component in an embodiment of a connector system for medical fluid administration.

The male connection member 300 has a proximal portion 310 and a distal portion 320. A lumen 315 is defined centrally through the male connection member with openings at the proximal portion, in order to allow connection to a tube, and at the distal end 321 of the distal portion 320, to allow liquid to pass through the connector.

An annular flange 330 extends radially outwards from the male connection member between the distal portion 320 and the proximal portion 310. The distal portion of the connector 320 has a substantially circular cross section and is tapered at 1.5 degrees such that the distal end of the distal portion has a slightly narrower diameter than a proximal end of the distal portion adjacent the flange 330.

A pair of longitudinally extending flanges 340, 350 extend from opposite sides of the proximal portion 310 of the male connection member.

The distal end 321 of the connection member comprises a pair of projections 360, 370 that project from an end surface 391. The projections 360, 370 are sculpted such that they project to the greatest degree at the radially outer-most point of the distal end 321 of the connection member, and incline inwards towards the centrally defined lumen. Furthermore, the end surface 391 of the distal end 321 of the connection member is dished such that there is an incline from the circumference 390 towards the centrally defined lumen 315.

Each of the projections 360, 370 is tipped with a tooth 375, 365. The cutting edge of each tooth 375, 365 is oriented to face the opposite circumferential direction to the other, i.e. the cutting edge of tooth 365 faces circumferentially clockwise and the cutting edge of tooth 375 faces a circumferentially anti-clockwise.

Figure 14:
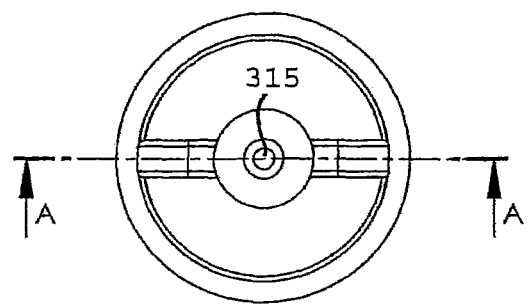
FIG. 14 illustrates a plan view of a connection made by the male connection member of FIG. 10 in engagement with the female connection member of FIG. 1.
Figure 15:
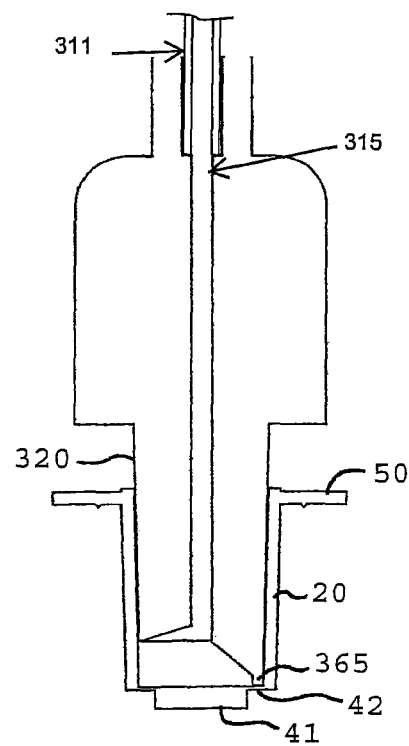
FIG. 15 is a sectional view of the connection made in FIG. 14.

A complete connector or connector system for medical fluid administration according to a specific embodiment will comprise both a male connection member and a female connection member as described above. FIG. 14 illustrates a plan view of a male connection member when coupled to a female connection member as described in FIGS. 1 and 2. FIG. 15 is a cutaway along the line indicated in FIG. 14 with FIG. 15 showing a tube or conduit 311 coupled to the proximal end of the male connection member.

In order to form a connection between a male connection member and a female connection member, for example to allow fluid contained within a vial to pass into a fluid administration set, then the male connection member must be inserted into the female connection member. The distal portion of the male connection member is dimensioned to mate with and provide an interference seal with the internal surface of the sheath of the female connection member. The taper of 1.5 degrees in the sheath is mirrored in the taper of the male connection member and this taper allows the connection member to be inserted its full length into the sheath before a seal is made.

Once inserted into the sheath, contact is made between the terminal teeth 365, 375 of the male connection member and the peripheral region of the septum 42. As the material forming this region of the septum is thin, the application of a small amount of pressure to the male connection member both forms a seal with the walls of the sheath and causes the terminating teeth to penetrate the peripheral region of the septum. By simultaneously twisting the male connection member and pushing the male connection member further into the sheath, the septum is ruptured to allow communication between the lumen 315 of the male connection member and the contents if the container.

When the male connection member is twisted the terminal teeth 365, 375 catastrophically disrupt the thin peripheral region of the septum 42. As the male connection member is forced further into the septum the inclined projections or castellations 360, 370 engage with the thickened region in the center of the septum and tilt this thickened region, thereby providing greater stress to the remaining portion of peripheral region of the septum and further aiding the catastrophic rupture of the septum.

Figure 16:
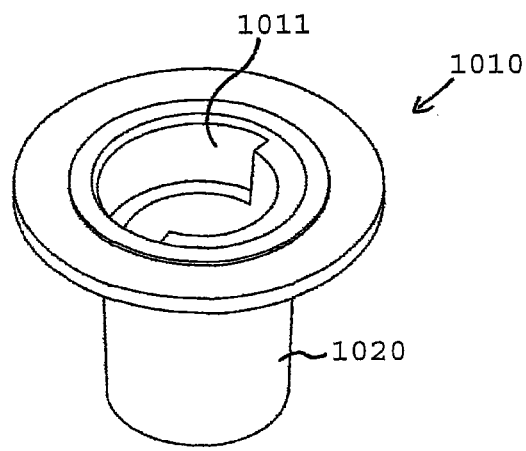
FIG. 16 is a perspective view of a fourth embodiment of a female connection member for a connector system for medical fluid administration.
Figure 17:
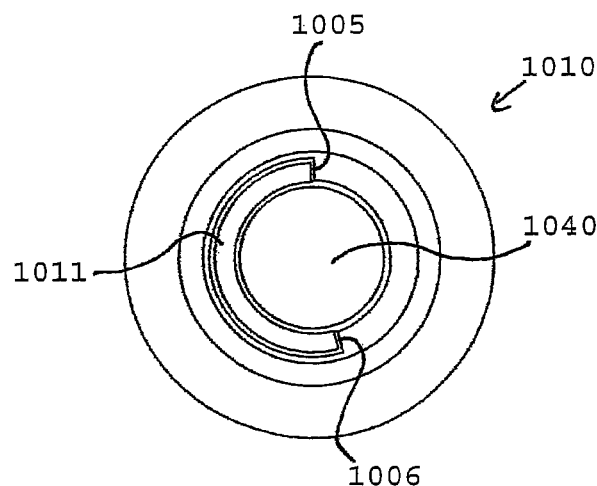
FIG. 17 is a plan view of the female connection member of FIG. 16.
Figure 18:
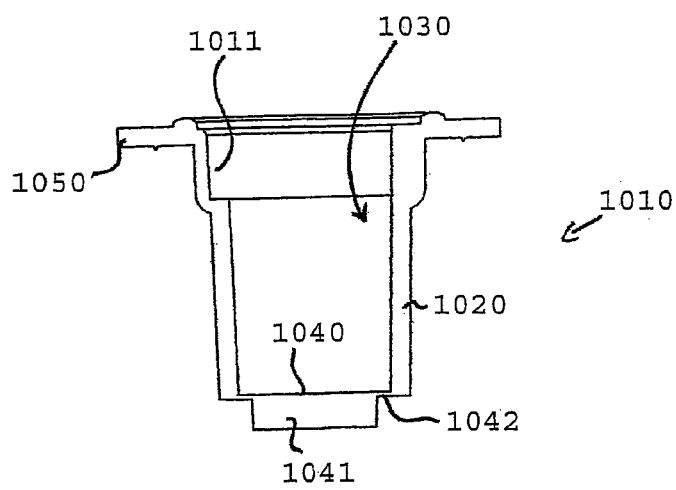
FIG. 18 is a cross-sectional view of the female connection member of FIG. 16.

FIGS. 16 to 18 illustrate a fourth embodiment of a female connector or female connection member 1010. The female connection member 1010 may be used as a component in an embodiment of a connector system for medical fluid administration. The female connection member 1010 of FIGS. 16 to 18 incorporates a keyway 1011 for receiving a key defined in a male connection member.

Figure 19:
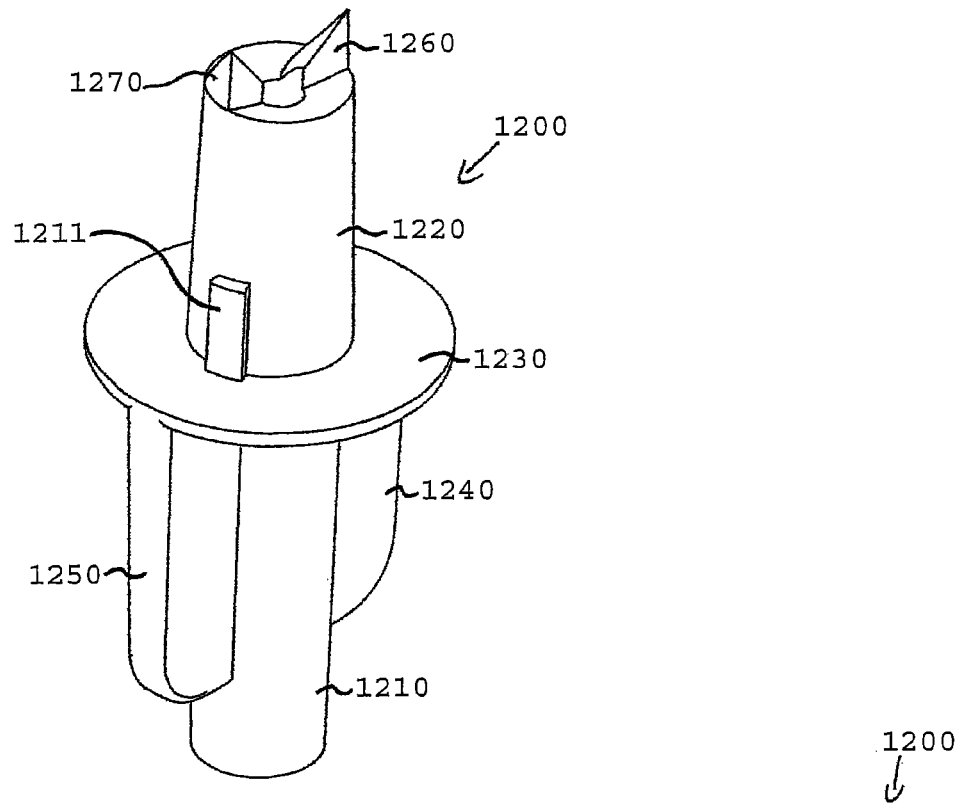
FIG. 19 is a perspective view of a second embodiment of a male connection member for connection with the female connection member of FIG. 16 in a connector system for medical fluid administration.
Figure 20:
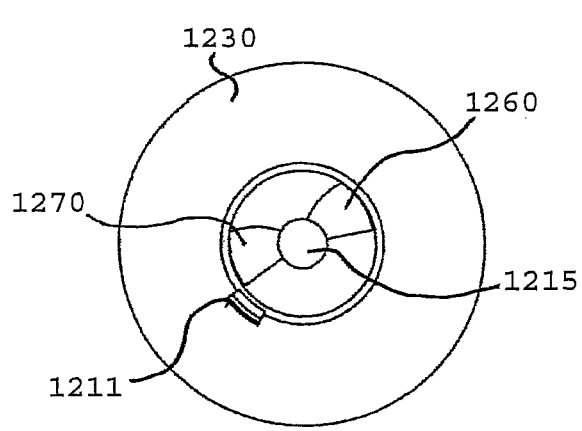
FIG. 20 is a plan view of the male connection member of FIG. 19 from the distal end showing a plan view of offset projections and a key associated with the proximal portion of the male connection member.

FIGS. 19 and 20 illustrate a second embodiment of a male connection member 1200. The male connection member 1200 may be used as a component in an embodiment of a connector system for medical fluid administration. The male connection member 1200 comprises a key 1211 for engaging with a keyway of a female connection member.

The second embodiment of a male connection member 1200 is preferably used for coupling with the female connection member 1010 of FIGS. 16 to 19 in a connector system according to a specific embodiment of the invention.

With reference to FIGS. 16 to 18, the female connection member 1010 has a body 1020 formed from an injection-moulded polypropylene. The body 1020 defines a sheath 1030 having a substantially circular cross-section. A proximal end of the sheath defines an opening for receiving a male connection member, and a distal end of the sheath is spanned by a septum 1040. An annular flange 1050 extends radially outwards from an uppermost or proximal end of the sheath.

The septum comprises a central region or central portion 1041 formed from a thick section of polypropylene and a peripheral section or peripheral portion 1042 formed from a thin section of polypropylene. The central portion 1041 has a thickness of 1.80 mm and the peripheral portion has a thickness of 0.25 mm. The length of the female connection member from the radial flange 1050 to the distal end of the sheath is 14.75 mm.

The body 1020 of the female connection member at its proximal end defines a keyway that extends downwardly into an upper portion of the sheath 1030. The keyway 1011 extends around 170° of an upper portion of the circumference. The keyway extends to a depth of 5 mm from the proximal end of the sheath 1030.

The female connection member 1010 may be used as an access port, for example as an access port to an infusion bag or bottle as illustrated in relation to other specific embodiments of the invention.

FIGS. 19 and 20 illustrate a male connector or male connection member 1200 for connecting with the female connection member 1010 in a connector system for medical fluid administration according to an embodiment of the invention.

The male connection member has a proximal portion 1210 and distal portion 1220. The male connection member 1200 further comprises a lumen 1215, an annular flange 1230, a pair of longitudinally extending flanges 1240, 1250, and a pair of projections 1260, 1270.

The male connection member 1200 of FIGS. 19 and 20 further comprises a key 1211 formed from a section of material that extends radially outward from the distal portion 1220. The key is a portion of material defined and extending from the proximal portion of the male connection member that has a length of 5 mm, a width of 2.5 mm, and a thickness of 1 mm. The key 1211 acts to prevent the proximal portion 1220 of the male connection member 1200 from being inserted into a female connection member that is otherwise dimensioned to make a sound connection but is lacking a keyway to receive the key.

The projections 1260, 1270 are not circumferentially-evenly-spaced on the distal end of the male connection member. Rather than being directly opposing the second projection (i.e. having an angular separation of 180° from the second projection), the first projection 1260 has an angular separation of 170° from the second projection 1270.

In order to form a connection, the male connection member 1200 is inserted into the female connection member 1010. The male connection member 1200 cannot be inserted into the female connection member 1010 until the male connection member is oriented such that the key 1211 on the distal portion of the male connection member is aligned with the keyway 1011 defined in the female connection member 1010. The distal portion 1220 of the male connection member 1200 is dimensioned to mate within an inner surface of the sheath 1030 of the female connection member 1010. At a point of near maximum insertion of the male connection member into the female connection member the projections 1260, 1270 engage with the peripheral portion 1042 of the septum and pierce it. The male connection member 1200 is then twisted within the female connection member 1010. The extent of this twisting is restricted, however, by the interaction of the key 1211 on the male connection member 1200 and the keyway 1011 on the female connection member 1010. By twisting the male connection member anticlockwise until the key abuts a first end-point 1006 of the keyway 1011 and then clockwise until the key abuts a second end-point 1005 of the keyway, the projections cut through a portion of the peripheral portion of the septum. If the keyways allow a 170° rotation of the male connection member and the projections are offset by an angle of 170°, the full range of twisting of the male connection member within the female connection member will result in 340° of the peripheral regional of the septum being ruptured. The remaining 20° that is not ruptured acts as a retaining hinge that retains the central portion 1041 in connection with the female connection member 1010 after a connection has been made.

The keyway may allow a greater or lesser angular rotation than 170°. For example, the keyway may allow a 175° rotation or a 180° rotation or a 185° rotation. As long as the two projections 1260 and 1270 are offset by a small degree, it is possible to rotate the male connection member within the female connection member through a defined angle and cut or rupture the peripheral portion of the septum for a substantial, but not entire, portion of its circumference, thereby leaving a portion of the peripheral region of the septum to connect the central portion of the septum with the female connection member after a connection has been made.

Figure 21:
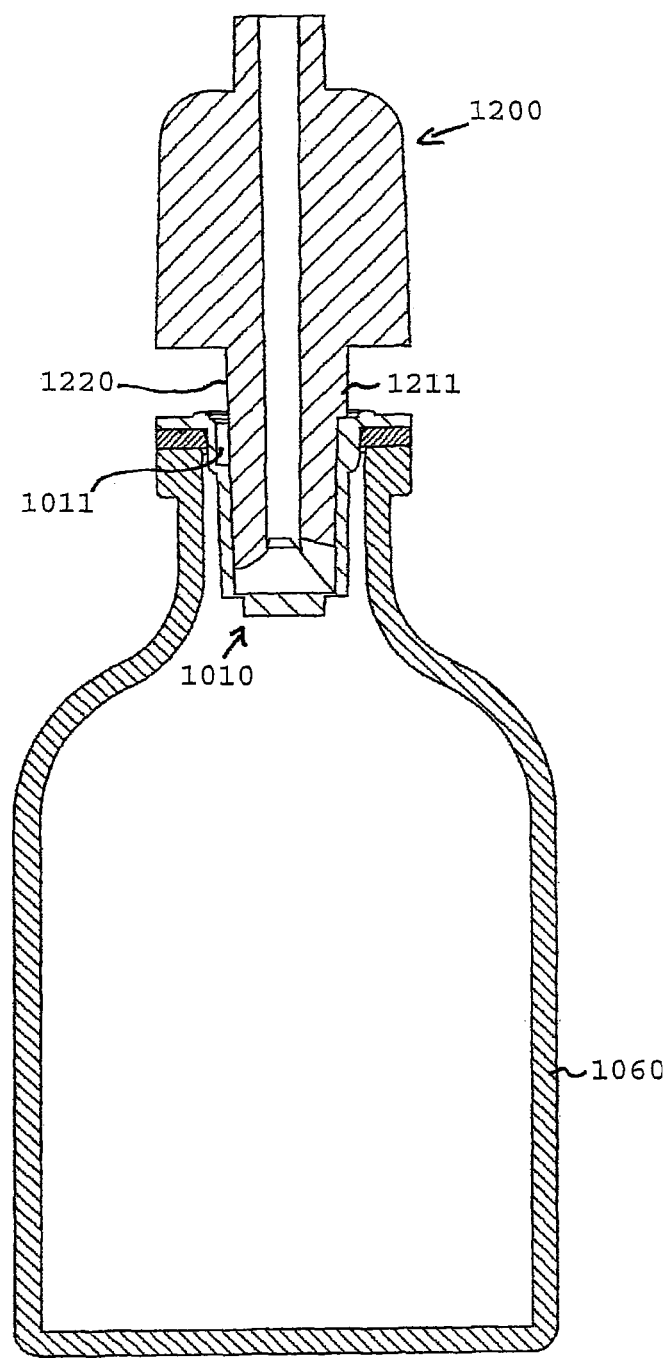
FIG. 21 illustrates a cross-sectional side view of the connector system for medical fluid administration comprising a female connection member as illustrated in FIG. 16 and a male connection member as illustrated in FIG. 19.

FIG. 21 illustrates the use of a female connection as illustrated in FIGS. 16 to 18 as an access port in a vial of medical fluid 1060, a male connection member 1200 as illustrated in FIGS. 19 and 20 is arranged such that its distal portion 1220 is partially inserted into the sheath of the female connection member 1010. The male connection member 1200 in the illustrated orientation cannot fully connect with the female connection member, as the male connection member is oriented such that the key 1211 is not aligned with the keyway 1011 defined in the female connection member.

Figure 22:
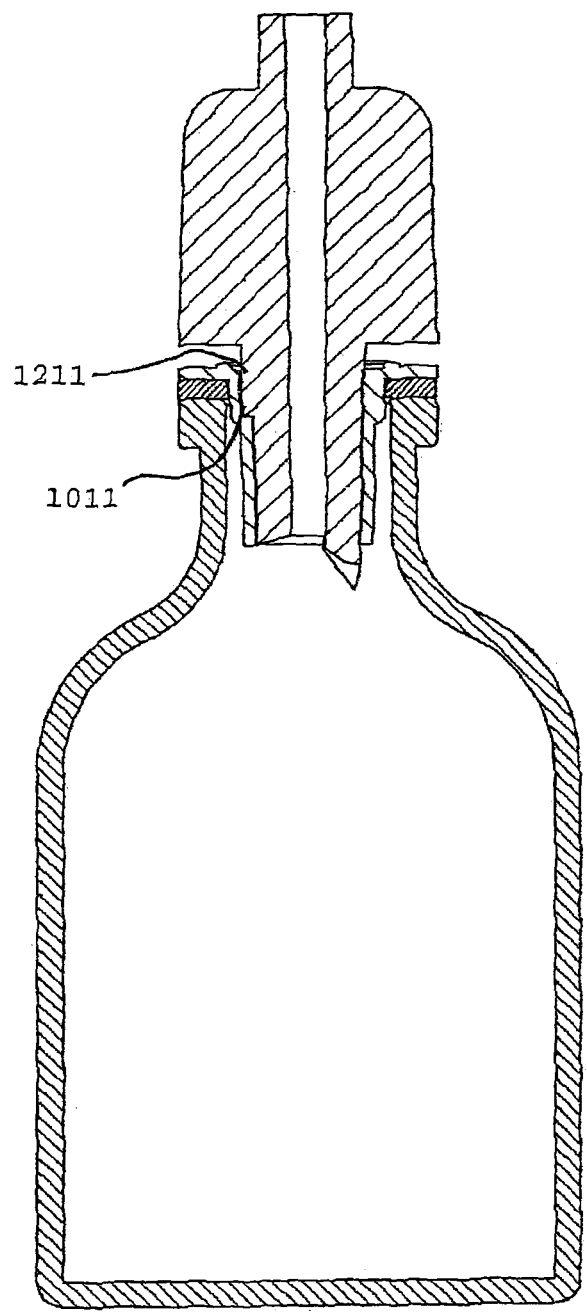
FIG. 22 illustrates a cross-sectional side view of the connection system illustrated in FIG. 21 after a connection has made.

FIG. 22 illustrates the male connection member 1200 in the correct orientation, such that the key 1211 and keyway 1011 are in alignment allowing a connection to be made.

In summary, any one of the specific embodiments of female connection members described above would be unsuitable for forming a connection with a standard giving spike or with a hypodermic needle. The thickened central portion of the septum for each of these female connection members is designed to prevent the accidental insertion of a hypodermic needle or giving spike. Were a healthcare professional to angle a hypodermic needle such that was able to penetrate through the thinner peripheral region of the septum, then this region of the septum would not grip the needle to form a competent seal. If a healthcare professional forces either a hypodermic needle or a giving spike into the thickened portion of the septum, then a catastrophic failure of the entire septum would occur at its outer-most annular region forming a leak that prevents a competent connection being made.

In the specific embodiments, the dimensions of the sheath of the female connection members are sufficiently wide to prevent an interference seal being formed with the body of a standard giving spike. Thus, a healthcare professional cannot accidentally form a competent connection to a medical fluid container closed by a female connection member according to an embodiment of the invention.

The specific embodiments of a male connection member described above are uniquely adapted for forming a connection with one or more of the described female connection members. Furthermore, the male connection members of the specific embodiments could not accidentally form a connection with a medical bottle or vial containing fluid closed with a standard rubber septum. The male connection members specifically described are highly unlikely to penetrate a standard rubber septum for closing a vial, and even if they did, this penetration would not allow a seal to be formed by which passage of fluid within the vial could pass into the lumen at the central portion of the male connection member.

Furthermore, the male connection members specifically described above are dimensioned such that they do not physically fit into the standard ports usually used for allowing access to a standard universal giving spike. Thus, it should not be possible for a healthcare professional to accidentally connect a conduit or administration set terminating in a male connection member according to an embodiment of the invention with a medical container fitted with standard closures.

Both the male connection member and the female connection member of a connector system according to an embodiment of the invention are designed to be compatible with each other, but not with other commonly used medical fluid connection members.

The invention claimed is:

1. A female connection member for a system for medical fluid administration,
    the female connection member defining a sheath for receiving a distal portion of a male connection member, a distal end of the sheath being spanned by a septum having a central region and a peripheral region, in which the central region of the septum is formed from material having a substantially greater thickness than a peripheral region of the septum surrounding the central region,
    the female connection member being configured to receive a male connection member having a body comprising a distal portion terminating in a distal end and a proximal portion terminating in a proximal end, a lumen being defined through the body for the passage of liquid from the distal end to the proximal end, in which the distal end of the male connection member comprises means for rupturing the peripheral region of the septum when the male connection member is received in the female connection member to form a connection,
    in which the female connection member comprises a retaining means for retaining the central region of the septum after the peripheral region of the septum has been ruptured by receiving the male connection member, and
    the female connection member defines a keyway for receiving a key extending from the distal portion of the male connection member, such that the female connection member can only receive the distal portion of the male connection member to form a connection when the key is aligned with the keyway.

2. A female connection member according to claim 1, in which the central region of the septum is formed from material having a thickness that is between 1.5 and 400 times thicker than material forming the peripheral region of the septum surrounding the central region.

3. A female connection member according to claim 1, in which the material forming the central region has a thickness of between 1 mm and 3 mm.

4. A female connection member according to claim 1, in which the distal end of the sheath is substantially circular in cross-section and has an internal diameter of between 8 mm and 15 mm.

5. A female connection member according to claim 1, in which the retaining means comprises a portion of material configured to connect the female connection member with the central region of the septum after the peripheral region of the septum has been ruptured.

6. A female connection member according to claim 1, in which the retaining means forms a hinge.

7. A female connection member according to claim 1, in which the retaining means comprises a portion of material extending radially between the distal end of the sheath and the central region of the septum, optionally in which the retaining means comprises a lug, flange or tab which projects longitudinally from the distal end of the sheath and in which the portion of material extends radially from the lug, flange or tab to connect with the central region of the septum.

8. A female connection member according to claim 1, in which the female connection member is configured to be disrupted over a portion of the circumference of the peripheral region so that the remaining non-ruptured portion of the peripheral region acts to retain the central portion of the septum, while still allowing a fluidic connection to be formed.

9. A female connection member according to claim 1, in which the keyway extends circumferentially around the female connection member for allowing the male connection member, when received in the female connection member, to rotate relative to the female connection member, the key extending from a distal portion of the male connection member interfering with the female connection member to restrict the rotation to a predetermined angle.

10. A female connection member according to claim 1, comprising a substantially annular flange extending radially outwards from the sheath enabling the female connection member to span an opening in a medical fluid container.

11. A female connection member according to claim 1, in which the female connection member forms an access port into a medical fluid container.

12. A female connection member for a system for medical fluid administration,
    the female connection member defining a sheath for receiving a distal portion of a male connection member, a distal end of the sheath being spanned by a septum having a central region and a peripheral region, in which the central region of the septum is formed from material having a substantially greater thickness than a peripheral region of the septum surrounding the central region,
    the female connection member being configured to receive a male connection member having a body comprising a distal portion terminating in a distal end and a proximal portion terminating in a proximal end, a lumen being defined through the body for the passage of liquid from the distal end to the proximal end, in which the distal end of the male connection member comprises means for rupturing the peripheral region of the septum when the male connection member is received in the female connection member to form a connection,
    in which the female connection member comprises a retaining means for retaining the central region of the septum after the peripheral region of the septum has been ruptured by receiving the male connection member, and
    the peripheral region of the septum does not form a complete ring around the central region, but extends around the central region sufficiently to result in a catastrophic failure around the periphery of the septum in preference to a puncture through the central region of the septum.

\* \* \* \* \*